United States Patent [19]

Kao

[11] B 3,985,834

[45] Oct. 12, 1976

[54] PHOSPHAZENE COMPOSITION

[75] Inventor: James T. F. Kao, Baton Rouge, La.

[73] Assignee: Ethyl Corporation, Richmond, Va.

[22] Filed: June 12, 1973

[21] Appl. No.: 369,221

[44] Published under the second Trial Voluntary Protest Program on February 24, 1976 as document No. B 369,221.

Related U.S. Application Data

[63] Continuation-in-part of Ser. No. 339,902, March 9, 1973, abandoned.

[52] U.S. Cl. .......................... 260/927 N; 260/973; 427/394
[51] Int. Cl.$^2$ .......................................... C07F 9/15
[58] Field of Search ...................... 260/973, 927 N

[56] References Cited
UNITED STATES PATENTS

| | | | |
|---|---|---|---|
| 2,681,295 | 6/1954 | Hamalainen | 260/927 N X |
| 3,294,872 | 12/1966 | Allcock | 260/973 X |
| 3,459,838 | 8/1969 | Klender | 260/973 X |
| 3,795,526 | 3/1974 | Bergeron | 260/927 N X |

*Primary Examiner*—Anton H. Sutto
*Attorney, Agent, or Firm*—Donald L. Johnson; John F. Sieberth; James M. Pelton

[57] ABSTRACT

A phosphazene composition is prepared by reacting a fully hydrocarboxylated phosphazene with a partially hydrocarboxylated phosphazene under conditions whereby an organic halide is evolved, in which at least one of the fully and partially hydrocarboxylated phosphazenes are prepared by adding an alkali metal hydrocarboxide to a phosphonitrilic halide whereby the final phosphazene composition contains some —P—ONa bonds, as well as —P—O—P—bond configurations. The phosphazene compositions are useful as fire retardants for cellulosics.

8 Claims, No Drawings

PHOSPHAZENE COMPOSITION

CROSS-REFERENCE TO RELATED APPLICATION

This application is a continuation-in-part of application Ser. No. 339,902, filed Mar. 9, 1973, now abandoned.

BACKGROUND OF THE INVENTION

Various materials made from phosphonitrilic chlorides are useful as fire retardants; U.S. Pat. Nos. 3,455,713, 3,505,087 and 3,532,526.

So far as is known, materials made by the process of this invention have not been heretofore described.

Polydichlorophosphazene linked by a P—O—P bond is depicted on
Page 138 of H. R. Allcock, *Phosphorus-Nitrogen Compounds*, Academic Press, New York, New York (1972), and
Page 317 of J. R. Van Wazer, *Phosphorus and Its Compounds*, *I* Interscience Publishers, Inc., New York, New York (1958).

Polymers having P—O—P bonds made by a different process are described on pages 97–8 of *Chemical Week*, Feb. 20, 1965.

Unfortunately, the phosphazene fire retardants of the prior art which are used to flame retard cellulosic materials, such as rayon, suffer from the disadvantage of washing out of the final textile fabric. So far as is known, prior art phosphazene fire retardants, except at high loading usually greater than 26 weight percent, have been unable to pass the stringent requirements of Federal Standards, for example, the Children's Sleepwear Standard (DOC FF 3-71) published in Federal Register, Vol. 36, No. 146, pp. 14062–14066, on July 29, 1971. Now for the first time, phosphazene fire retardants according to this invention which are used to flame retard rayon not only pass the Children's Sleepwear Standard, but do so at concentrations which are commercially acceptable. The phosphazenes of this invention do not adversely affect other advantageous properties of rayon.

SUMMARY OF THE INVENTION

The invention encompasses four major aspects: modified phosphazene polymers, their production, cellulose fibers containing them and a method of preparing the fibers.

Thus, one embodiment of this invention is in a process of (a) heating a phosphonitrilic halide with at least a stoichiometric amount of an alkali metal compound of the formula MOR, wherein M is an alkali metal and R is an organic radical having up to about 8 carbon atoms to produce a phosphonitrilate polymer, (b) reacting a phosphonitrilic halide with less than the stoichiometric amount of said alkali metal compound producing a phosphonitrilate polymer containing a substantial amount of residual halide groups, and (c) heating the phosphonitrilate polymer of (a) with the phosphonitrilate polymer containing a substantial amount of residual halide groups of (b) under conditions sufficient to drive off an organic halide, the improvement comprising preparing at least one of the polymers of (a) and (b) by a process of adding said alkali metal compound to said phosphonitrilic halide, said phosphonitrilic halide being contained in a hot inert solvent such that during the reaction a substantial excess of said phosphonitrilic halide is maintained, whereby the viscosity of the resultant phosphonitrilate polymer and its average molecular weight are increased.

A second embodiment comprises the product produced by this process.

A third embodiment comprises regenerated cellulose filaments and fibers containing a flame retardant amount of such product.

Another embodiment comprises a method for preparing a cellulose filament which comprises mixing a flame retardant product of this invention with viscose and shaping, coagulating and regenerating said filament from said viscose-containing mixture.

DESCRIPTION OF PREFERRED EMBODIMENTS

Starting materials for a process of this invention are phosphazenes of four types, of which the first is a fully or substantially fully substituted phosphazene represented by the formula

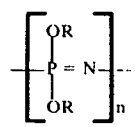

where $n$ is at least three and R is an organic, preferably a hydrocarbyl group or halogen substituted hydrocarbyl group. Preferably R is of up to about eight carbon atoms. R can be alkyl, cycloalkyl, alkenyl, alkaryl, aralkyl, or aryl. Examples of such groups designated by R are methyl, ethyl, n-propyl, isopropyl, n-butyl, cyclohexyl, cyclopentyl, 1-propenyl, 1-pentenyl, 2,3-xylyl, phenyl, naphthyl, benzyl, and the like. The radicals may have one or more halogens such as the radicals chloropropyl, chloroethyl, chlorophenyl, 2,3-dichloropropyl, 1,3-dichloropropyl, and the brominated and fluorinated derivatives thereof.

The second type of organophosphazene used in this process is represented by the formula

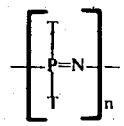

wherein $n$ is at least 3 and T is selected from chlorine, bromine and OR wherein R has the same significance as above, such that from about 80 to about 95 weight percent of the T groups are —OR and the remainder is halogen.

The third and fourth type of phosphazenes used in this invention have a small but significant amount of alkali metal replacing some of the R groups in the two types of phosphazenes mentioned above. Thus, a number of —P—OM bond configurations are formed, such that from about 5 to about 60 weight percent of the phosphazene is the alkali metal as a —P—OM group.

All four types of phosphazenes can be prepared by reacting metal alcoholates or phenolates with a phosphonitrilic halide. Preferably, the metal alcoholates and phenolates have the formula MOR, wherein R is an organic radical, and M is an alkali metal, such as sodium or potassium. More preferably the sodium alcoholates and phenolates are used.

It is not necessary to use pure phenolates or alcoholates. Mixtures can be used as sodium butoxide - sodium ethoxide - sodium propoxide or sodium phenolate - sodium propoxide, for example. Three, four or more materials can be used in the mixtures and the relative concentration of each ingredient can be varied as desired.

The phosphonitrilic halides used to prepare the phosphazenes have the formula $(PNX_2)_n$ where $n$ is at least 3 and X is preferably chlorine or bromine. Usually, the phosphonitrilic halides used are mixtures but pure materials can be used, if desired. The halides can be cyclic trimer, tetramer or higher cyclic polymer, linear polymer, or mixtures thereof. The molecular weight can be from 350 to 10,000 or more, preferably from about 350 to about 5000.

The phosphonitrilic chlorides can be obtained by reacting ammonia or ammonium chloride with phosphorus pentachloride:

$$nPCl_5 + nNH_4Cl \rightarrow (PNCl_2)_n + 4 nHCl$$
$$nPCl_5 + nNH_3 \rightarrow (PNCl_2)_n + 3 nHCl$$

Methods for conducting these processes have been described in U.S. Pat. Nos. 3,367,750 and 3,656,916, for example. These patents are incorporated by reference herein as if fully set forth.

Phosphonitrilic chlorides can also be obtained by:
reacting ammonia with phosphorus and chlorine, U.S. Pat. No. 3,658,487, and
reacting phosphorus trichloride, chlorine, and ammonium chloride; U.S. Pat. No. 3,359, 080.

These patents as well as *Am. Chem. J.* 19 782 (1897), *Ber.* 57 B, 1343 (1924), U.S. Pat. Nos. 2,788,286, 3,008,799, 3,249,397, 3,347,643, 3,372,005, 3,378,353, 3,379,511, 3,407,047, 3,462,247, Netherlands Pat. No. 70,05128, and *J. Chem. Soc.* (A) pp. 768–772 are incorporated by reference herein as if fully set forth.

A preferred method for preparing phosphonitrilic halides for use in this invention may be described as follows: Phosphorus pentachloride slurried in monochlorobenzene is charged to a reactor. The reactor is sealed and gaseous HCl introduced with agitation to assist solution of the HCl in monochlorobenzene. The reactor is pressurized with from about 10 to about 40 psig with gaseous HCl. Ammonia is then introduced at a rate not less than 0.13 liters per minute per mole of $PCl_5$ and heat is applied to raise the temperature of the reaction mixture to 110°C to 150°C during this initial ammonia feed. The hydrogen chloride pressure will fall at first; and additional hydrogen chloride can be added to maintain the desired pressure. However, this is not essential if the initial pressure is at least 10 psig at the start of ammonia feed since by-product hydrogen chloride will be produced before all of the preadded hydrogen chloride is used up. The reaction between ammonium chloride and $PCl_5$ initiates at about 60°C. The temperature rises to about 110°-140°C. The feed rate of ammonia is reduced after about ½ hour and held to a rate of from about 0.05 to about 0.13 liters per minute per mole of $PCl_5$. This rate is continued for about three hours, or depending upon the amount fed until at least the stoichiometric amount of ammonia is added. After the ammonia has been fed into the reaction, the temperature is maintained for about 1 hour at between 110°-150°C, preferably from 120°C to 130°C under pressure from 10-40 psig and preferably about 20 psig. This heating period finishes the reaction by allowing traces of unreacted material to react. After about 1 hour the pressure is released and heating is continued for another ½ hour at reaction temperature. This allows any remaining hydrogen chloride dissolved in the solvent to be removed.

The product of this reaction is generally 65–75 percent cyclic phosphonitrile chloride polymers and 35–25 percent linear materials. In general, the cyclic distribution ranges from 60–75 percent trimer, 18–24 percent tetramer, and 7–12 percent of pentamer. The product yield ranges upward of 90 percent, based on the amount of phosphorus used. Yields higher than 92 percent are not uncommon. In contrast, products of prior art processes have cyclic products ranging from 80–85 percent cyclic using lower feed rates followed by higher feed rates of ammonia. Moreover, the traditional process for producing phosphonitrile chloride using a solid ammonium chloride of commercial grade and a halogenated aliphatic hydrocarbon solvent produces a generally higher molecular weight product consisting of about 50 percent cyclics and about 50 percent linears.

EXAMPLE I

To a glass reactor equipped with stirrer, a reflux condenser and a means for heating the reactor contents was charged 208.3 grams (1.0 mole) of phosphorus pentachloride in 312.5 grams of monochlorobenzene. The reactor was sealed and anhydrous hydrogen chloride was fed into the reactor with stirring until the pressure of the reactor was about 15 psig. A total of 7.6 grams (0.208 mole) of hydrogen chloride was added to the reactor. Gaseous ammonia was then introduced to the reactor at a rate of 0.182 liters per minute per mole of phosphorus pentachloride while the reactor contents were heated at a rate of 2.5°C per minute using a heating mantle on the reactor. The ammonia feed rate was dropped to 0.0908 liters per minute per mole of phosphorus pentachloride after about 5.46 liters (0.241 mole) of ammonia was fed into the reactor over a period of about 30 minutes. The temperature was controlled at 130°C and pressure at 20.0 psig. The ammonia feed was stopped when a total of 22 liters (1.0 mole) was fed into the reactor. The heating and stirring was continued for one hour at 20 psig, and for another 30 minutes at atmospheric pressure. The total reaction time was 5½ hours. The reactor contents were then cooled to room temperature and discharged from the reactor by nitrogen pressure. About 400 grams of clear product solution was obtained. Analysis by vapor phase chromatograph showed that the solution contained 26.6 percent phosphonitrilic chlorides of which 63.3 percent were cyclic compounds with the following distribution: trimer — 73 percent, tetramer — 20 percent and pentamer — 7 percent. The recovered yield was 92 percent, based on phosphorus pentachloride.

EXAMPLE II

The procedure of Example I was repeated, except that a total of 22.8 liters (1.047 mole) of ammonia was fed to the reactor and the initial heating rate was 1.5°C per minute. The reaction was initiated at 65°C as observed by a sudden change in the rate of temperature increase. The reaction mixture was heated to 130°C over two hours period and held at that temperature for 3 hours. The product slurry, about 392.5 grams, was obtained after 5½ hours reaction time. Vapor phase chromatograph analysis of the product showed 67.7 percent cyclic phosphonitrilic chloride polymers having the following distribution: trimer — 64 percent, tetramer — 24 percent, pentamer — 12 percent. The recovered yield of total product was 92 percent, based on phosphorus pentachloride.

The procedure of Example I was repeated with different reaction times and temperatures. Ammonia was fed at the same rate with 10 percent excess (1.1 mole total) (Examples III and IV) to 2 percent short (0.98 mole total) (Example V). The results of these experiments are shown in the following table.

TABLE I

PREPARATION OF PHOSPHONITRILIC CHLORIDE

| Example | Reaction Temp. °C | Reaction Time hrs. | Percent Product Distribution | | | Percent Cyclics | Percent Yield |
| --- | --- | --- | --- | --- | --- | --- | --- |
| | | | Trimer | Tetramer | Pentamer | | |
| III | 120 | 7½ | 65 | 20 | 15 | 75 | 85 |
| IV | 140 | 4½ | 73 | 18 | 9 | 77 | 74 |
| V | 150 | 4 | 90 | 8 | 2 | 50 | 80 |

The reaction between the phosphonitrilic halide and the alkali metal alcoholate or phenolate is carried out so that some of the alkali metal is reacted and incorporated into the resulting phosphazene. Preferably, this result can be accomplished by adding the alkali metal alcoholate or phenolate to the phosphonitrilic halide. Without limiting the invention to any particular theory or mechanism, it is believed that the large initial concentrations of the phosphonitrilic halide present cause the formation of —P—ONa bonds on the phosphazene. Of course, the large majority of groups incorporated in the phosphazene will be OR groups. However, a small but significant amount of the alkali metal detected on analysis of the phosphazenes which is not removable by washing with water and which is not affected during the subsequent reaction of the fully substituted phosphazene and the partially substituted phosphazene confirms the incorporation of the alkali metal into the phosphazene.

The amount of alkali metal incorporated into the phosphazene should be sufficient to aid in dispersing the phosphazene into viscose, but not so great as to affect the properties of the viscose of the retention of the phosphazene in the fiber. Preferably from about 0.1 to about 5 weight percent of alkali metal, as —P—ONa bonds, can be used in the present invention. More preferably from about 0.5 to about 2 weight percent can be employed.

The reaction between phosphonitrilic halide and metal alkoxide or phenoxide is preferably conducted in the presence of a liquid to facilitate contacting the reactants. Preferred reaction media are exemplified by hexane, heptane, ligroin, benzene, toluene, the xylenes, monochlorobenzene, and propanol.

As indicated above, the phosphazenes are preferably prepared by adding to phosphonitrilic halide, an alkali metal alcoholate or phenolate. It is preferred, when preparing the fully or substantially fully substituted phosphanzene, that the alkali metal derivative be in substantial excess over the theoretical requirement. By a substantial excess is meant an excess of at least about 5 weight percent. It is convenient to use amounts of alkoxide or aryloxide which are from about 5 to about 15 weight percent excess over the theoretical requirement.

In many instances, the reaction is rapid and exothermic at the beginning and requires no heating. After mixture of the reactants is complete it may be convenient to heat the resultant reaction mass and hold it at reflux temperature for such time as analysis indicates complete reaction. Reaction times in the range of from ½ to 10 hours can be used. This is somewhat dependent upon the reaction temperature which is usually within the range of from ambient to 110°C; more preferably from about 55°C to about 110°C.

After conduction of the reaction, the excess free alkali metal alcoholate or phenolate compound and the solvent are removed by distillation or other suitable means. These can be recycled for later use.

As with the preparation of the metal derivative of the hydroxy compound the phosphazene synthesis proceeds well at ambient pressure. Accordingly, atmospheric pressure is of choice. However, greater or lesser pressures can be used if desired.

When preparing mixed phosphazenes, a mixture of metal derivatives of two or more hydroxy compounds is added to the phosphonitrilic halide. Thus, for example, one can prepare mixed propoxyphosphazenes by reacting the sodium derivative of a mixture of normal- and isopropyl alcohols. In a similar fashion, mixed ethoxybutoxy phosphazenes and mixed butoxyphosphazenes can also be prepared. In like manner, the phosphazenes may be derived from two or more phenols or can be prepared from mixtures of phenols and alcohols. A typical example of the latter type is the product obtained by reacting phosphonitrilic chloride with a 1:1 mixture of sodium methoxide and sodium phenoxide.

It is to be understood that mercaptides can be used in a fashion similar to that described above to prepare the sulfur compounds analogous to the above-described phosphazenes.

After removal of the free alcoholate or phenolate compound by water-washing, it is convenient to isolate the product from the resultant mass by stripping the remainder of the solvent. In many instances, best results are obtained by using a plurality of water washes. In many instances, two washes will suffice. For precaution against emulsions during washing, it is preferred to have the water washes conducted such that the water has a pH of 9 or higher. Water-washing is employed by mixing the phosphazene product with water and agitating. Typical agitating times are 10 to 20 minutes but shorter or longer times can be employed, if desired. If in the first water wash, a rag layer appears, it can be left with the organic layer for a subsequent wash. If emulsion appears in the second wash, sodium chloride or other salt can be added to increase the density difference between the phases.

After water-washing and separating, the organic layer can be subjected to distillation to remove solvent. Distillation can be conveniently conducted at reduced pressure, say, 20–30 mm Hg. All or substantially all solvent can be removed in this manner; alternatively, the bulk of residual solvent can be removed by other means such as a Rodney Hunt wiped film evaporator.

The following typical procedure is illustrative but non-limiting.

EXAMPLE VI

A. Take a 4000 gallon, glass-lined reactor equipped with heating, cooling, stirring, and condensing means as well as a vent routed through a water scrubber to remove by-product HCl. Clean and dry the vessel and purge it with nitrogen. Charge 17,150 pounds of monochlorobenzene and activate the stirring means. Add 10,268 pounds of $PCl_3$ and activate cooling means.

Feed chlorine into the vapor phase in the reactor such that a total of 5210 pounds is admitted. Keep the addition rate such that the reactor temperature is at a 25°C maximum and the reactor pressure is below 5 psig. The addition of chlorine will take about 4–6 hours. The $PCl_3$ produced is utilized in the following way.

B. Break the vacuum with nitrogen and add 5210 pounds of $NH_4Cl$ below 80 microns in size. Seal the reactor and heat to reflux (approximately 130°C) for 8 hours. Vent the HCl gas evolved to the water scrubber.

Thereafter (the reaction is more than about 50 percent complete) slowly distill monochlorobenzene until 10,500 pounds have been removed. The reactor is maintained at 125°–135°C until reaction is complete as determined by virtual cessation of HCl evolution and by demonstrating the equal volumes of reaction mass and cyclohexane (or undecane) yield only one liquid phase.

Procedures (A) and (B) are repeated and the two batches are combined. Centrifugation is conducted (using a centrifuge capable of 800 G operation) to remove excess $NH_4Cl$. The $NH_4Cl$ can be recycled.

The filtrate is stripped to remove 13,400 pounds of monochlorobenzene which is held for recycle. Then, 15,355 pounds of toluene are added to the product. The yield is 16,200 pounds of neat phosphonitrilic chloride from each two-batch lot.

C. Melt 495 pounds of sodium at 110°C. Heat 1580 pounds of toluene to the same temperature. Add the molten sodium to the hot toluene in a suitable vessel. To the hot mixture add 1480 pounds of propanol. By metering the $H_2$ evolution, add the propanol at such a rate that no more than about 150 pounds of unreacted propanol is present. Maintain the reaction mixture hot enough to avoid sodium solidification. Two to four hours is required for the propanol addition.

The reaction is maintained at reflux until hydrogen evolution has substantially ceased (and the sodium reacted to substantial completion). About 1–3 hours will be required after the completion of the propanol addition. The sodium propylate produced is utilized as below.

D. The toluene phosphonitrilic chloride mixture (2270 pounds) is added to the sodium propylate. The sodium propylate is a 10 percent excess over the theoretical requirement based on recovered $PNCl_2$. Initially, the reaction is rapid and exothermic and requires no heating. After all of the $PNCl_2$ has been added the mixture is heated to reflux (approximately 107°C) and held for 3–6 hours until the reaction is shown to be complete by VPC analysis.

Fifty gallons of propanol and toluene are removed from the reaction mixture by distillation. This is recycled back to the next batch of sodium propylate. The quantity of fresh propanol feed is adjusted for the composition of the recycle stream. The product is cooled to 60°C.

E. The first water wash consists of 375 gallons of water. The agitator is turned on for 15 minutes, then shut off and the mixture is allowed to settle for 30 minutes. The water layer is withdrawn. Any rag layer is left with the organic layer for the second wash or can be discarded, as desired. The second wash consists of 100 gallons of water. The contents are agitated for 15 minutes. The mixture is allowed to separate and the water layer is withdrawn. If an emulsion forms at this point, sodium chloride is added to increase the density difference between the phases.

At this point, 2715 pounds of solvent and a small quantity of n-propanol is stripped from the hexapropoxyphosphazene (HPP) at 20–30 mm Hg and < 80°C. A forecut of 250 pounds is taken to remove residual water. The distillate is collected and the forecut is discarded. About 10 percent solvent remains in the HPP following this stripping operation. The product is fed to a Rodney-Hunt wiped-film evaporator where the remainder of the solvent is stripped from the HPP at 5–10 mm Hg, 100°C (the final product contains < 1.0 percent solvents). The HPP is stored in 350 gallon portable containers from which it is filtered and packaged for shipping. The solvent is transferred to the distillation columns where the MCB and toluene are separated for recycle.

EXAMPLE VII

A. To a clean, dry, nitrogen-flushed 10 gallon glass-lined reaction vessel, charge 41.5 pounds of dry monochlorobenzene (MCB) and 25.68 pounds of $PCl_3$. Pressure the vessel to 10 psig with nitrogen, then evacuate to 200 mm and shut off the vacuum system from the vessel. Chlorine (13.4 pounds) (1 percent excess) gas is added above the surface of the stirred liquid. This reaction is exothermic and it is necessary to cool the reaction to hold the temperature below 25°C. However, do not cool below 5°C as $PCl_3$ will crystallize out and the chlorination will not be complete. White solid $PCl_5$ separates from the MCB solution. Near the end of the reaction, permit a positive pressure of 10 pounds of chlorine on the reactor. When the theoretical weight of chlorine has been added, remove a sample of the liquid layer and analyze for $PCl_3$.

B. Add dry ammonium chloride (11.0 pounds or 10 percent excess) to the $PCl_5$ slurry in the 10 gallon glass-lined vessel. Seal the vessel, mix and introduce nitrogen over the surface of mixture to assist in HCl removal. Slowly heat to 125°C removing all materials distilling up to 105°C with $N_2$ in the head space. The rate of heating is determined by the rate of HCl evolved. Attach the top of the condenser to a HCl scrubber and measure the HCl evolved by weighing the HCl scrubber. Reaction will start between 95°–115°C depending on $NH_4Cl$ particle size. When about 10–15 percent of the HCl gas has been evolved, start the addition of ammonia gas to the reactor at such a rate as to maintain an excess of HCl gas being evolved from the reactor. Add a total of 3.5 pounds of $NH_3$ gas (10 percent excess). Use a capillary dipleg, maintain a $N_2$ stream through the dipleg until the $NH_3$ feed has begun. At the completion of the $NH_3$ feed, resume nitrogen feed — at all times have a gas stream through the dipleg. Sample during the last part of the HCl evolution for analysis. Test material for complete cyclization after HCl evolution is complete by mixing an equal volume of the $PNCl_2$ solution, as is, with an equal volume of cyclohexane. If one phase remains, then the reaction is ready for the next step.

Filter the mixture to remove the excess NH₄Cl, wash the filter with MCB, and then dry and use this NH₄Cl in the next run. Strip off the MCB at 50°–55°C (20 mm Hg absolute) until a thick stirrable slurry remains. Add the minimum amount of toluene to the mixture to effect complete solution.

Illustrative of the preparation of a substantially fully substituted phosphazene using the addition of the metal alcoholate or phenolate to the phosphonitrilic halide is the following example.

EXAMPLE VIII

To a suitable reactor were charged 1452 grams of normal octane and 218.1 grams of sodium. The reactor contents were heated to 105°C until the sodium melted and then started the stirrer to disperse sodium droplets in the octane. Then 598.4 grams of normal propyl alcohol were fed into the reactor with evolution of hydrogen as the reaction takes place. Heating was simultaneously discontinued and the exothermic reaction maintained temperature. The reaction was nearly quantitative and produced about 759 grams of sodium propoxide.

This sodium propoxide slurry was added to 1895 grams of phosphonitrilic chloride solution in monochlorobenzene, of which about 24 weight percent was phosphonitrilic chloride. The temperature of the reaction mixture was 120°C and the sodium propoxide was added over a 2.5 hour period. The reaction mixture was heated for 3 hours after sodium propoxide feed ceased.

The product was washed with water and the solvent distilled off leaving a hexapropoxyphosphazene product having the following characteristics:

| | |
|---|---|
| P, wt % | 18.9 |
| N, wt % | 8.62 |
| Total Cl, wt % | 0.11 |
| Na, wt % | 1.6 |
| Molecular wt | 768 by vapor phase osmometer |
| Viscosity at 25°C | 350 cp |
| Solubility, | |
| in water - 0.65 wt % P | |
| in 0.5 wt % NaOH solution - 0.59 wt % P | |

The fully substituted phosphazenes may contain residual halogen from incomplete substitution of alkoxy or aryloxy groups. Thus, the phosphazene can have up to 2 weight percent chlorine and, as designated herein, be substantially fully substituted.

The partially substituted phosphazene is prepared in the same way except that some of the halogen atoms in the phosphonitrilic halide are left unsubstituted. In other words, less than all the halogen atoms are displaced. In general, when preparing the partially substituted phosphazene, one uses from about 10 to about 97 weight percent of the stoichiometric amount of the hydroxy compound or metal derivative thereof. Greater or lesser amounts can be used. More preferably, from about 60 to about 95 weight percent of the stoichiometric amount is used. In a highly preferred embodiment, about 80–95 weight percent of the stoichiometric amount is employed.

The phosphazenes can have a number average molecular weight of 500 up to 1000, 3000, 5000, 10,000 or more. Preferably, materials having a molecular weight of from about 500 to about 10,000 are used. More preferably, they have a molecular weight of 500–8000.

Illustrative of the preparation of a partially substituted phosphazene made by adding the alkali metal alcoholate or phenolate to the phosphonitrilic halide are the following examples.

EXAMPLE IX

To a 500 cc, 3-necked glass reaction flask was added 357 grams of normal octane. 53.76 grams of metallic sodium were cut from a sodium brick and divided into small pieces. The sodium pieces were added to the reactor and the contents heated to 105°C until the sodium melted and then started the stirrer to disperse into the octane as fine droplets. To the dispersion was added 154 grams of normal propanol over a 20 minute period. The heating was discontinued as the exothermic reaction maintained the temperature of 105°C. The hydrogen evolved was vented and the reaction continued until all of the sodium reacted. This took about 20 minutes after propanol feed was discontinued. The practically quantitative reaction produced sodium propoxide in octane.

A solution of phosphonitrilic chloride (176.2 g) in monochlorobenzene (448 g) was prepared in a suitable reaction vessel, the final solution being 28.2 weight percent phosphonitrilic chloride. The solution can be heated to 105°C or at room temperature. The sodium propoxide-octane slurry was added to the phosphonitrilic halide solution and the reaction mixture heated at 105°C for 3 hours with stirring.

The reactor contents were cooled to room temperature and washed twice with water, first with 440 ml resulting in the washwater having pH of 8 and then with 100 ml of water resulting in the wash-water having a pH of 9. The separations between product and water layer were good with little emulsion or rag layer formed. Then the solvent was distilled off at 80°–100°C.

Analysis of the product (201 g) showed the following weight percentages of product on vapor phase chromatograph:

| | | |
|---|---|---|
| pentachloropropoxyphosphazene | 1.30 | wt % |
| tetrachlorodipropoxyphosphazene | 3.37 | |
| trichlorotripropoxyphosphazene | 5.35 | |
| dichlorotetrapropoxyphosphazene | 13.44 | |
| monochloropentapropoxyphosphazene | 3.43 | |
| hexapropoxyphosphazene trimer | 0.43 | |
| octapropoxyphosphazene tetramer | 0.77 | |

The viscosity of the product was 167 centipoise at 25°C and total chloride content was 10.8 weight percent.

EXAMPLE X

Following the procedure of example IX another run was made, except that after addition of the sodium propoxide slurry to the phosphonitrilic chloride solution the reaction mixture was heated for 3.5 hours. Only one water-wash with 440 ml of water was used.

The product, weighing 203 grams, had a viscosity of 173 centipoise at 25°C and a total chloride analysis of 10.1 weight percent. Vapor phase chromatographic analysis showed the following distribution:

| | | |
|---|---|---|
| pentachloropropoxyphosphazene | 0.61 | wt % |
| tetrachlorodipropoxyphosphazene | 2.96 | |
| trichlorotripropoxyphosphazene | 4.93 | |
| dichlorotetrapropoxyphosphazene | 11.89 | |
| monochloropentapropoxyphosphazene | 4.39 | |

-continued hexapropoxyphosphazene trimer      0.50

When the crosslinking reaction of fully and partially substituted phosphazenes is conducted, equal weights of the two reactants can be used, but it is not necessary to do so. A weight excess of either reactant can be employed. Only an amount of halogen, preferably chlorine, on the partially substituted phosphazene sufficient to give the desired amount of crosslinking is required.

Crosslinking is achieved by reaction of the halogen atom with alkoxy or aryloxy groups, for example, to form an alkyl halide or aryl halide. Although not bound by any theory, it is believed the product of this reaction can be illustrated by the following:

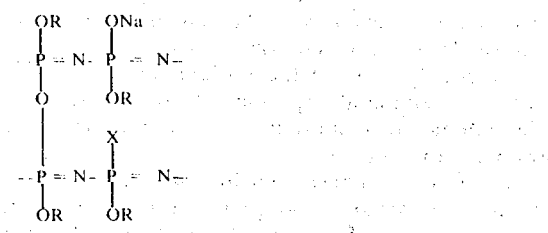

The P—O—P bond illustrated was formed by splitting out R—Cl. The —P—ONa bond is not substantially affected by the crosslinking reaction.

There are two ways to achieve the amount of halogen desired in the reaction mixture:
a. Use a relatively large amount of a partially substituted phosphazene containing a relatively small amount of halogen, and
b. Use a relatively small amount of a partially substituted phosphazene containing a relatively large amount of halogen.

Of course, any combination of these two methods can be used such as an intermediate amount of a partially substituted phosphazene containing an intermediate amount of halogen. Also, any combination of two or more halogen-containing phosphazenes can be employed and one can use any residual halogens on the substantially fully substituted phosphazene.

Using any of these means alone or in combination, it is usually desirable that the reaction mixture contain from 1–30 weight percent chlorine, preferably 1–17 and more preferably 2–12 weight percent. The partially substituted phosphazene is preferably peaked at dichlorotetrapropoxyphosphazene, which is a more reactive crosslinking species.

In general, mildly elevated temperatures are employed. In general, reaction temperatures are usually higher than that required to react alcoholate, phenolate, alcohol, or phenol with phosphonitrilic chloride. Good results are achieved if the temperature is within the range of from about 80° to about 220°C; somewhat higher and lower temperatures can be used. A preferred temperature range is from about 90° to about 190°C.

The heating time is not critical. The temperature is somewhat dependent on the inherent ability of the starting materials to react and the time is also dependent on the degree of reaction desired. In general, longer heating times, as higher heating temperatures cause greater amount of crosslinking or viscosity increase. Thus, with a minor amount of routine experimentation a skilled practitioner can determine the reaction temperature and time required to give the desired amount of reaction or viscosity increase. In general, heating times of ½–120 minutes afford good results; from about 3 to about 60 minutes are preferred. However, times as long as 3 hours or more can be used.

The reaction can be conducted in the presence of an inert liquid reaction medium such as toluene or other hydrocarbon, but it is not necessary to do so. Similarly, the reaction can be conducted in the presence of an inert atmosphere such as nitrogen or argon, but it is unnecessary to do so.

The reaction can be conducted at ambient pressure. However, superatmospheric and subatmospheric pressures can be used if desired. Subatmospheric pressures during the course of or after the reaction can assist removal of volatile components evolved. Preferred subatmospheric pressures are 0.1 to 180 mm Hg.

EXAMPLE XI

In this run a phosphonitrilate polymer was produced by crosslinking hexapropoxyphosphazene made by adding the phosphonitrilic chloride to the sodium propoxide (as illustrated in Examples VI and VII) with a partially propoxylated phosphazene made by adding the sodium propoxide to the phosphonitrilic chloride (as illustrated in Examples IX and X).

To a suitable reaction vessel was added 133.3 grams of hexapropoxyphosphazene of the following analysis:

| | | |
|---|---|---|
| P, wt % | 18.5 | |
| N, wt % | 9.15 | |
| Total Cl, wt % | 0.69 | |
| Na, wt % | 0.0 | |
| Viscosity at 25°C | 77.4 | cp |
| Number Average Molecular Wt | 695 | | and 66.7 grams of the partially substituted phosphazene of Example IX. The reactor contents were heated to 175°C with stirring for 1.5 hours under 10–20 mm of Hg vacuum. From the reactor 16.8 grams of propyl chloride was evolved, condensed and collected. The reaction product was cooled to room temperature.

The following analysis of the product was made:

| | | |
|---|---|---|
| P, wt % | 19.3 | |
| Total Cl, wt % | 0.75 | |
| Na, wt % | 0.18 | |
| Molecular weight, vapor phase osmometer | 864 | |
| Viscosity at 25°C | 775 | |
| Vapor phase chromatographic analysis | | |
| tetrachlorodipropoxyphosphazene | 0.69 | wt % |
| monochloropentapropoxyphosphazene | 0.72 | wt % |
| hexapropoxyphosphazene trimer | 10.0 | wt % |
| unknown X | 0.24 | wt % |
| octapropoxyphosphazene tetramer | 2.33 | wt % |

EXAMPLE XII

The procedure of Example XI was followed except that the hexapropoxyphosphazene was prepared according to Example VIII and equal weights of the fully and partially substituted phosphazenes were reacted.

To a suitable reaction vessel was added 80 grams of the partially substituted phosphazene prepared in Example IX and 80 grams of the fully substituted phosphazene prepared in Example VIII. The reaction mixture was heated to 145°C with stirring and held at that temperature for 1 hour. A sample, marked A, was taken. The temperature was increased to 153°C and maintained for 1 hour. Another sample, marked B, was taken. The temperature was increased to 165°C and held for 1 hour. A final sample, marked C, was taken. Throughout the heating propylchloride was evolved, condensed and collected.

The results and analysis of the three samples is given below:

|  | A | B | C |
|---|---|---|---|
| Appearance | Cloudy | Cloudy | Less Cloudy |
| Color | Pale straw | Pale straw | Pale brown |
| Viscosity at 25°C | Thin | Thin | 13,000 cp |
| Molecular weight by vapor phase osmometer | 990 | 1081 | 1196 |
| Vapor Phase Chromatographic Analysis, wt % |  |  |  |
| tetrachlorodipropoxyphosphazene | 1.4 | 1.3 | 1.13 |
| trichlorotripropoxyphosphazene | 0.74 | — | — |
| dichlorotetrapropoxyphosphazene | 2.57 | 0.61 | — |
| monochloropentapropoxyphosphazene | 1.83 | 1.40 | 1.26 |
| hexapropoxyphosphazene trimer | 14.83 | 10.42 | 7.12 |

EXAMPLE XIII

To a suitable reaction vessel was added 70 grams of the fully substituted phosphazene of Example VIII and 76 grams of the partially substituted phosphazene of Example X. The reactor contents were heated to 145°C with stirring and held at that temperature for 1 hour and 15–60 mm Hg vacuum. The temperature was increased to 155°C and held for 1.5 hours at less than 15 mm Hg. The reaction produced propyl chloride which was collected and condensed, amounting to 5.7 g during the first hour and 5.5 grams during the second 1.5 hours. The reaction product was cooled to room temperature.

Analysis indicated the following:
P, wt % — 21.2
Total Cl, wt % — 2.43
Soluble Cl, wt % — 0.88
Viscosity at 25°C — 3091 cp
Molecular weight by vapor phase osmometer — 1005

EXAMPLE XIV

A large scale run was made following the procedure of Example XI. The phosphazenes had the following characteristics:

|  | Partially Substituted (made by addition of NaOC$_3$H$_7$ to PNCl$_2$) | Fully Substituted (made by addition of PNCl$_2$ to NaOC$_3$H$_7$) |
|---|---|---|
| P, wt % | 19.44 | 18.5 |
| N, wt % | 8.79 | 8.48 |
| Total Cl, wt % | 11.18 | 0.37 |
| Viscosity at 25°C | 93 cp | 87.7 cp |
| Molecular weight | 592 |  |

To the reactor was added 2400 grams of each of the above phosphazenes. The reactor contents were heated to 145°C with stirring and the temperature held for 1 hour at 17.5–19 mm Hg vacuum. A sample of the reaction product after heating 1 hour had a viscosity of 230 cp at 25°C. The temperature was increased to 155°C and held for 1 hour under vacuum. A sample of the reaction product had a viscosity of 452 cp at 25°C. The temperature was further increased to 165°C and held for 1 hour. Then the reaction mixture was cooled to room temperature. The total propyl chloride evolved from the reactor was 364.0 grams.

Analysis of the reaction product was as follows:
P, wt % — 21.4
N, wt % — 9.89
Total Cl, wt % — 1.47
Na, wt % — 0.13
Viscosity at 25°C — 2266 cp
Solubility in water — 0.16 wt % P
Solubility in 0.5 wt % NaOH solution — 0.54 wt % P Similar results are obtained when the substantially fully propoxylated and the partially propoxylated reactants are made from
phosphonitrilic chloride produced by the processes of Examples I–IV, and
phosphonitrilic chloride produced by the processes of Examples V–VI, herein.

Similar results are obtained when the substantially fully and partially propoxylated phosphazene reactants have molecular weights of from about 350 to about 4000 and the partially propoxylated phosphazene has a chlorine content equivalent to 80–95 weight percent of said T groups are propoxy, and the remainder are chlorine.

Similar results are obtained when the fully and partially substituted phosphazenes have instead of propoxy groups
a. ethoxy groups
b. n-butoxy groups
c. ethoxy and n-butoxy groups (50-50 mixture by weight)
d. phenoxy groups
e. n-heptoxy groups
and the reaction is conducted at temperatures of from 90°–190°C and the total weight percent chlorine in the substantially fully and partially substituted phosphazene is from 1–17 weight percent.

Thus, a preferred embodiment of the process of this invention is one in which the fully substituted phosphazene is prepared by adding said alkali metal compound to said phosphonitrilic halide. Another preferred embodiment according to this invention is one in which the partially substituted phosphazene is prepared by adding the alkali metal compound to the phosphonitrilic halide. In a most preferred embodiment of the invention both the fully substituted and partially substituted phosphazene compounds are prepared by adding the alkali metal compound to the phosphonitrilic halide. These phosphazenes may then be reacted to drive off an organic halide forming the phosphonitrilate polymer of this invention which have increased molecular weight, increased viscosity and P—ONa bonds which aid the incorporation of the polymer into various materials.

Illustrative of this embodiment is the following large scale run in which both the fully and partially substituted phosphazenes are prepared by adding the alkali metal compound to the phosphonitrilic halide.

EXAMPLE XV

To a 5000 ml flask was added 2400 grams each of the phosphazene products made substantially according to Examples VIII for the fully substituted phosphazene, and IX or X for the partially substituted phosphazene. The phosphazenes had the following characteristics:

|  | Partially Substituted (made by addition of NaOC₃H₇ to PNCl₂) | Fully Substituted (made by addition of NaOC₃H₇ to PNCl₂) |
|---|---|---|
| P, wt % | 18.9 | 18.6 |
| N, wt % | 8.79 | 8.45 |
| Total Cl, wt % | 11.18 | 1.10 |
| Na, wt % | 0.12 | 0.65 |
| Molecular weight | 592 | 653 |
| Viscosity at 25°C, cp | 93 | 91.5 |

The reactor contents were heated to 120°C and a vacuum was drawn on the reactor to about 100 mm Hg. The temperature was increased to 145°C and the temperature and vacuum maintained for 1 hour. The temperature was increased to 155°C at a pressure of about 105 mm Hg vacuum and these conditions were held for about 30 minutes. Then the reactor temperature was increased to 165°C at a pressure of 100 mm Hg vacuum and these conditions were maintained for another 30 minutes. Then the reactor contents were cooled to about 40°–50°C while maintaining the vacuum. A sample taken after cooling had a viscosity of < 500 cp at 25°C This was not as high as desired. Therefore, the reactor contents were reheated to 165°C at about 100 mm Hg vacuum and these conditions were held for 30 minutes. A sample drawn from the reactor had a viscosity of 541 cp at 25°C. The temperature of the reactor was increased to 175°C and held for 30 minutes at 100 mm Hg vacuum. A sample drawn after this period was 1,148 cp at 25°C. The reactor contents were then cooled, while still maintaining the vacuum. A final sample of the condensed phosphonitrilate polymer had a viscosity of 2,490 cp at 25°C. Overall reaction time was 3.5 hours.

Upon removal of the reactor contents and analysis of the phosphonitrilate polymer produced, the following results were reported:

| P, wt % | 21.3 |
|---|---|
| N, wt % | 9.59 |
| Total Cl, wt % | 1.68 |
| Molecular Weight | 1001 |
| Viscosity at 25°C, cp | 3307 |
| Specific Gravity at 25°C | 1.18 |
| Gardner Color | 4 |

EXAMPLE XVI

A large scale run was made to produce a product similar to that of Example XV. In this example three batches of phosphonitrilate polymer were prepared from phosphonitrilic chloride by adding sodium propoxide thereto such that about 10 weight percent of Cl remains on the partially substituted phosphonitrilate polymer, for example, following the procedure of Examples IX or X. Also two batches of fully substituted phosphonitrilate polymer were prepared according to Example VIII by adding the sodium propoxide to the phosphonitrilic chloride. These five batches of phosphonitrilate polymer had the following characteristics:

| Batch | A | B | C | D | E |
|---|---|---|---|---|---|
| P, Wt % | 20.3 | 19.7 | 18.8 | 18.9 | 19.9 |
| N, Wt % | 9.37 | 9.03 | 8.50 | 9.03 | 8.75 |
| Total Cl, Wt % | 10.44 | 8.30 | 2.38 | 1.12 | 10.49 |
| Na, Wt % | 0.15 | 0.10 | 0.30 | 0.39 | 0.11 |
| Specific Gravity | 1.17 | 1.14 | 1.08 |  |  |
| Viscosity at 25°C, cp | 95 | 90 | 81 |  |  |
| Acid Number | 6.38 | 5.39 |  | 0.3 | 3.8 |
| Gardner Color | 5 | 4–5 | 6–7 |  |  |

To a suitable reactor were added the following weights of the above phosphonitrilate polymers:

| Phosphonitrilate Polymer | Weight, lbs. |
|---|---|
| A | 35 |
| B | 30 |
| C | 65 |
| D | 65 |
| E | 65 |

The reactor contents were heated with stirring under vacuum of 120 mm Hg up to about 135°C during a period of about 30 minutes. The temperature continued to increase up to about 160°C over the next 3.5 hours. The heating was discontinued and full vacuum of about 10 mm Hg was drawn on the reactor during cooling over a 45 minute period.

The condensed phosphonitrilate polymer analyzed as follows:

| P, wt % | 21.6 |
|---|---|
| N, wt % | 9.79 |
| Total Cl, wt % | 2.06 |
| Na, wt % | 0.25 |
| Viscosity at 25°C, cp | 1593 |
| Molecular weight | 963 |
| Specific Gravity | 1.17 |
| Gardner Color | 5 |
| Acid Number | 9.0 |
| Solubility in H₂O | 0.17 wt % P |
| in 0.5% NaOH | 0.29 wt % P |

Materials prepared by the process described and exemplified above can be used as flame retardant agents for cellulose materials including fibers, filaments, fabrics and films. The materials can be added by dipping, spraying, or other means utilized for treating the surface.

Alternatively, for rayon and other regenerated cellulosics, the fire retardant may be impregnated or added to the product by incorporation in the viscose prior to spinning. The amount of fire retardant can be from about 1 to about 30 weight percent and preferably from about two to about 20 weight percent.

For impregnation prior to spinning and the finished materials, one may refer to Godfrey U.S. Pat. No. 3,455,713. That patent is incorporated by reference herein as if fully set forth. Thus, one method of cellulose filaments and filamentary articles according to this invention is to use the flame retardants provided herein according to the method of Godfrey supra. Likewise, the instant invention provides regenerated cellulose fibers, filaments, filamentary articles and fabrics prepared from the flame retardants herein provided utilizing the techniques set forth by Godfrey.

After incorporation into the fiber or filament by spinning, the regenerated cellulose fiber containing the phosphonitrilate polymer of this invention passes through the spin bath containing sulfuric acid and is then washed to remove any residual acid from the spin bath. Subsequent treatment can include desulfurizing, rinsing, bleaching, washing, pH adjustment, rinsing and finally drying after application of a lubricant. Such finishing treatments are used on both filament and staple fiber production machines with operations tailored to the type of product produced. Finally, the fiber is scoured and dyed usually according to the end users specifications and procedures. The scoured and dyed fiber is then woven or knit into the desired textile material.

U.S. Government standards require the flame retardant rayon textile fabric to be washed 50 times and still retain its flame retardance. This standard is set forth for fabric used in Children's Sleepwear commonly known as DOC FF 3-71. The standard is based on a vertical burn test with the char length of the specimens and time of continued burning of molten drips or other fragments in the specimen as the acceptance criteria. The standard requires that the test must be met by the item in new condition and after 50 cycles of washing and drying in household machines.

The phosphonitrilate polymers of this invention were added to viscose solution and spun into fibers for flammability testing. The fiber was processed normally and tests were made on the fiber after washing the yarn, after scouring and dyeing and after being knit into a textile fabric. The tests were made according to the Children's Sleepwear Standard (DOC FF 3-71). The results of the testing are given in the following table:

FLAMMABILITY TESTING (DOC FF3-71)

| Ex. No. | Wt % Loading in Rayon | % P Retained in Rayon | | After Scour and Dye | Average Char Length, inches | | |
|---|---|---|---|---|---|---|---|
| | | Acid Free Yarn | Washed Yarn | | After 10 Wash Cycles | After 25 Wash Cycles | After 50 Wash Cycles |
| XIV | 13.0 | 98 | 77 | F* | — | — | — |
| | 16.7 | 95 | 80 | F | 6.1 | 4.0 | 5.5 |
| | 18.0 | 92 | 85 | F | 1.4 | 2.0 | — |
| | 20.0 | 94 | 81 | 1.6 (1.7)** | 0.5 (1.3) | 1.0 (0.9) | 0.3 (1.1) |
| | 23.1 | 94 | 81 | 1.1 (1.3) | 0.3 (1.1) | 0.5 (1.1) | 0.5 (1.1) |
| XV | 13.0 | 100 | 77 | F | — | — | — |
| | 16.7 | 98 | 85 | 4.3 | 4.5 | 3.3 | 4.4 |
| | 18.0 | 95 | 87 | F | 2.0 | 1.4 | — |
| | 20.0 | 98 | 89 | 0.7 (1.4) | 1.4 (1.3) | 1.2 (1.8) | 1.0 (1.3) |
| | 23.1 | 96 | 88 | 0.9 (1.5) | 1.0 (1.2) | 1.0 (1.1) | 0.8 (0.9) |
| XVI | 13.0 | 95 | 83 | — | — | — | — |
| | 16.7 | 94 | 88 | F | 3.2 | 3.0 | — |
| | 18.0 | — | — | — | — | — | — |
| | 20.0 | 89 | 84.4 | 1.6 | 1.0 | 1.1 | — |
| | 23.0 | 88 | 83.2 | — | — | — | — |

\* - Failure, the char length of sample was more than 10 inches.
\*\* - Numbers in parentheses indicate testing in a second laboratory.

Preferred modified phosphazene fire retardant products of this invention have a number average molecular weight of from about 900 to about 15,000.

From the above results, it can be seen that the phosphonitrilate polymers of this invention provide effective flame retardance even after 50 washing cycles for rayon fiber and filament. The failure of samples after scouring and dyeing is unexplainable especially in view of the fact that several samples although failing after scouring and dyeing pass the test after 50 launderings. Even in concentrations as low as 16.7 weight percent loading in the rayon fabric the material provided excellent flame retardance.

What is claimed is:

1. In a process for the preparation of a fire retardant phosphonitrilate polymer consisting essentially of the steps of (a) heating a phosphonitrilic halide with at least a stoichiometric amount of an alkali metal compound of the formula MOR, wherein M is an alkali metal and R is a hydrocarbyl or halogen-substituted hydrocarbyl radical having up to about 8 carbon atoms to produce a phosphonitrilate polymer, (b) reacting a phosphonitrilic halide with less than the stoichiometric amount of said alkali metal compound producing a phosphonitrilate polymer containing a substantial amount of residual halide groups and (c) heating the phosphonitrilate polymer of (a) with the phosphonitrilate polymer containing a substantial amount of residual halide groups of (b) under conditions sufficient to drive off an organic halide, whereby the viscosity of the resultant phosphonitrilate polymer and its average molecular weight are increased, the improvement comprising preparing at least one of the polymers of (a) and (b) by a process of adding said alkali metal compound to said phosphonitrilic halide, said phosphonitrilic halide being contained in an inert solvent such that during the reaction a substantial excess of said phosphonitrilic halide is maintained.

2. A phosphonitrilate polymer prepared according to the process of claim 1.

3. A process according to claim 1 wherein only the polymer of (a) is prepared by means of said improvement.

4. A process according to claim 1 wherein only the polymer of (b) is prepared by means of said improvement.

5. A process according to claim 1 wherein both the polymers of (a) and (b) are prepared by means of said improvement.

6. A process of claim 1 wherein said alkali metal is sodium and said alkali metal compound is selected from sodium alkoxide or phenoxide.

7. A process of claim 1 wherein said alkali metal compound is sodium propoxide.

8. A process of claim 1 wherein said phosphonitrilic halide is phosphonitrilic chloride.

* * * * *